(12) United States Patent
Rajamani et al.

(10) Patent No.: US 10,362,992 B2
(45) Date of Patent: Jul. 30, 2019

(54) SYSTEM AND METHOD FOR DETECTION OF MOTION IN DYNAMIC MEDICAL IMAGES

(71) Applicant: General Electric Company, Schenectady, NY (US)

(72) Inventors: Kumar Rajamani, Bangalore (IN); Sandeep Narendra Gupta, Niskayuna, NY (US); Rakesh Mullick, Bangalore (IN); Dattesh Dayanand Shanbhag, Bangalore (IN)

(73) Assignee: General Electric Company, Schenectady, NY (US)

( * ) Notice: Subject to any disclaimer, the term of this patent is extended or adjusted under 35 U.S.C. 154(b) by 205 days.

(21) Appl. No.: 15/101,538

(22) PCT Filed: Sep. 5, 2014

(86) PCT No.: PCT/US2014/054244
§ 371 (c)(1),
(2) Date: Jun. 3, 2016

(87) PCT Pub. No.: WO2015/084446
PCT Pub. Date: Jun. 11, 2015

(65) Prior Publication Data
US 2016/0310082 A1    Oct. 27, 2016

(30) Foreign Application Priority Data

Dec. 4, 2013   (IN) .......................... 5587/CHE/2013

(51) Int. Cl.
*A61B 5/055*   (2006.01)
*A61B 5/00*    (2006.01)
(Continued)

(52) U.S. Cl.
CPC .......... *A61B 5/7207* (2013.01); *A61B 5/0044* (2013.01); *A61B 5/055* (2013.01);
(Continued)

(58) Field of Classification Search
USPC ......................................................... 600/431
See application file for complete search history.

(56) References Cited

U.S. PATENT DOCUMENTS

| 5,275,163 A | 1/1994 | McKinnon et al. |
| 7,536,219 B2 | 5/2009 | Mitschke |

(Continued)

FOREIGN PATENT DOCUMENTS

| CN | 101238979 A | 8/2008 |
| CN | 101273277 A | 9/2008 |
| CN | 102483850 A | 5/2012 |

OTHER PUBLICATIONS

International Search Report and Written Opinion for International Application No. PCT/US14/54244, dated Dec. 24, 2014, 12 pages.
(Continued)

*Primary Examiner* — Nicole F Lavert
(74) *Attorney, Agent, or Firm* — Andrus Intellectual Property Law, LLP (57) ABSTRACT

A system and method for detecting motion is presented. The system and method includes identifying a region of interest in the plurality of images corresponding to a subject of interest. Furthermore, the system and method includes determining signal characteristics corresponding to the region of interest. In addition, the system and method includes generating a composite signal, where the composite signal comprises an aggregate of the signal characteristics corresponding to the region of interest. The system and method also includes analyzing the composite signal to detect motion in the region of interest.

25 Claims, 5 Drawing Sheets

(51) Int. Cl.
*A61B 6/00* (2006.01)
*A61B 8/08* (2006.01)
*G01R 33/565* (2006.01)
*A61B 5/11* (2006.01)
A61B 6/03 (2006.01)
G01R 33/56 (2006.01)
G01R 33/563 (2006.01)

(52) U.S. Cl.
CPC .......... *A61B 5/1128* (2013.01); *A61B 5/7289* (2013.01); *A61B 6/5264* (2013.01); *A61B 8/5276* (2013.01); *G01R 33/56509* (2013.01); A61B 6/032 (2013.01); A61B 6/037 (2013.01); A61B 2576/00 (2013.01); G01R 33/5601 (2013.01); G01R 33/5608 (2013.01); G01R 33/56308 (2013.01)

(56) References Cited

U.S. PATENT DOCUMENTS

| | | | |
|---|---|---|---|
| 7,903,853 | B2 | 3/2011 | Muradyan et al. |
| 7,911,207 | B2 | 3/2011 | MacFarlane et al. |
| 8,170,313 | B2 | 5/2012 | Kendrick et al. |
| 8,401,616 | B2 | 3/2013 | Verard et al. |
| 8,427,153 | B2 | 4/2013 | Hu et al. |
| 8,442,287 | B2 | 5/2013 | Fordyce, II et al. |
| 2005/0113696 | A1 | 5/2005 | Miller |
| 2008/0058587 | A1* | 3/2008 | Boyden ................ A61B 5/0071 600/104 |
| 2008/0187180 | A1* | 8/2008 | Yui ...................... G01R 33/543 382/107 |
| 2008/0188747 | A1 | 8/2008 | Randall et al. |
| 2009/0003655 | A1 | 1/2009 | Wollenweber |
| 2009/0062651 | A1 | 3/2009 | Chomas et al. |
| 2009/0093807 | A1* | 4/2009 | Hyde .................. A61B 5/0071 606/34 |
| 2009/0281417 | A1 | 11/2009 | Hartmann et al. |
| 2011/0044524 | A1* | 2/2011 | Wang .................... G01R 33/54 382/131 |
| 2011/0105883 | A1 | 5/2011 | Lake et al. |
| 2012/0022395 | A1 | 1/2012 | Kinkingnehun et al. |
| 2014/0301622 | A1 | 10/2014 | Forman |

OTHER PUBLICATIONS

Gautam, R., et al., "An efficient, bolus-stage based method for motion correction in perfusion weighted MRI," 21st International Conference on Pattern Recognition (ICPR), pp. 145-148 (Nov. 2012).

Rajamani, K., et al., "Detection of abrupt motion in DCE-MRI," SPIE Digital Library, vol. 8314, pp. 1-7 (Feb. 23, 2012).

Zadicario, E., et al., "Image-Based Motion Detection: Using the Concept of Weighted Directional Descriptors," Engineering in Medicine and Biology Magazine, vol. 29, Issue 2, pp. 87-94 (Mar./Apr. 2010).

Machine Translation and First Office Action and Search issued in connection with corresponding CN Application No. 201480066503.7 dated Aug. 2, 2018.

* cited by examiner

SYSTEM AND METHOD FOR DETECTION OF MOTION IN DYNAMIC MEDICAL IMAGES

CROSS-REFERENCE TO RELATED APPLICATIONS

This is a national stage application under 35 U.S.C. § 371(c) of prior filed, co-pending PCT Patent Application No. PCT/US2014/054244, filed on Sep. 5, 2014, which claims priority to India Patent Application No. 5587/CHE/2013, filed on Dec. 4, 2013. The aforementioned applications are herein incorporated in their entirety by reference.

BACKGROUND

Embodiments of the present specification relate to imaging, and more particularly to the detection of motion in dynamic medical images.

In modern healthcare facilities, non-invasive imaging systems are often used for identifying, diagnosing, and treating physical conditions. Medical imaging encompasses different non-invasive techniques used to image and visualize the internal structures and/or functional behavior (such as chemical or metabolic activity) of organs and tissues within a patient. Currently, a number of modalities of medical diagnostic and imaging systems exist, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems.

In clinical practice, currently, two-dimensional (2D) medical images, three-dimensional (3D) medical images, and/or four-dimensional (4D) medical images are being routinely used for tracking contrast uptake, delivery of dose and to study time related variations of anatomy and physiology. Specifically, in Dynamic Contrast Enhanced MRI (DCE-MRI), the uptake of contrast is analyzed for understanding the perfusion characteristics and cell structure, which may be indicative of tumor properties.

As will be appreciated, the 4D acquisitions typically entail long scan times for the complete scan. By way of example, acquiring data during 4D magnetic resonance imaging (MRI) generally calls for scan times that run into several minutes. Furthermore, during such long scans, patients under observation may experience voluntary and/or involuntary motion. Patient motion is one of the major challenges in the interpretation of image data. Particularly, patient motion hampers and/or distorts the quality of acquisition of image data. Some examples of patient motion during a scan may include a rapid shift, which may be caused due to the patient coughing or sneezing, motion due to breathing, and the like. Additionally, patient discomfort during the scan may also result in poor quality of data acquisition.

It may therefore be desirable to detect the presence of any patient motion during the acquisition of image data. The detection of motion may in turn be employed to aid in determining a corrective course of action. More particularly, clinical workflow may be greatly enhanced if information regarding the detected motion and a quantification of the detected motion is provided to a clinician during the acquisition of the image data.

Early efforts for detecting patient motion during the scan procedure include use of feature based methods. Other currently existing techniques entail use of registration methods for detecting and correcting patient motion. However, the currently available methods for detecting and correcting patient motion tend to be computationally very intensive and time consuming. Additionally, use of these techniques may entail user intervention or call for a trained clinician.

Furthermore, certain techniques for the acquisition of image data entail use of a contrast agent. However, use of the contrast agent may adversely affect the detection of motion as uptake of the contrast agent may confound visual perception of motion. In addition, detection and correction of motion using the currently available techniques in the presence of contrast changes during the dynamic acquisition is a challenging task.

BRIEF DESCRIPTION

In accordance with aspects of the present specification, a method for automated detection of motion is presented. The method includes identifying a region of interest in each of a plurality of images corresponding to a subject of interest. Furthermore, the method includes determining signal characteristics corresponding to the region of interest in each of the plurality of images. Moreover, the method includes generating a composite signal based on the signal characteristics corresponding to the region of interest in each of the plurality of images. The method also includes analyzing the composite signal to detect motion in the region of interest.

In accordance with another aspect of the present specification, a system for automated detection of motion is presented. The system includes a motion detecting platform configured to identify a region of interest in each of a plurality of images corresponding to a subject of interest, determine signal characteristics corresponding to the region of interest in each of the plurality of images, generate a composite signal based on the signal characteristics corresponding to the region of interest in each of the plurality of images, analyze the composite signal to detect motion in the region of interest, and correct the detected motion.

In accordance with yet another aspect of the present specification, an imaging system is presented. The imaging system includes an acquisition subsystem configured to acquire image data corresponding to a subject of interest. Additionally, the imaging system includes a processing subsystem in operative association with the acquisition subsystem and configured to process the acquired image data, where the processing subsystem includes a motion detecting platform configured to identify a region of interest in each of a plurality of images corresponding to a subject of interest, determine signal characteristics corresponding to the region of interest in each of the plurality of images, generate a composite signal based on the signal characteristics corresponding to the region of interest in each of the plurality of images, and analyze the composite signal to detect motion in the region of interest.

DRAWINGS

These and other features, aspects, and advantages of the present specification will become better understood when the following detailed description is read with reference to the accompanying drawings in which like characters represent like parts throughout the drawings, wherein.

DETAILED DESCRIPTION

As will be appreciated medical images are routinely used for tracking contrast uptake, delivery of dose and to study time related variations of anatomy and physiology. However, the acquisition of these medical images typically entails long time periods for the complete scan. Furthermore, patient motion during these long scans may hamper the quality of image data acquisition. Systems and methods for the automated detection of motion presented hereinafter enhance clinical workflow by robustly detecting motion. In addition, the systems and methods aid in determining a course of action for correcting the detected motion. More particularly, the systems and methods for the automated detection of motion described hereinafter provide a framework for robust detection of any patient motion and quantification of an extent of detected motion.

Moreover, it may be noted that any motion experienced by a subject of interest such as a patient affects signal characteristics corresponding to an anatomical region of interest in the patient being imaged. This effect may be more prominently enhanced in certain regions or volumes within the anatomical region of interest. The motion of organs in the patient alters the signal characteristics across time when there is considerable motion. Additionally, the motion of the patient also results in variations in the signal characteristics. In accordance with aspects of the present specification, the signal characteristics corresponding to an anatomical region of interest being imaged may be monitored and evaluated to detect any perceivable changes or variations in the signal characteristics. The exemplary methods and systems aid in determining if motion has occurred during a scan and also facilitate quantification of an extent of the detected motion. Moreover, the detected motion may aid in compensating for the patient motion, thereby enhancing the quality of image data acquisition and improving the efficiency of clinical workflow. It may be noted that patient motion may include a rapid shift, a rotational motion, a lateral motion, an elastic motion, and the like.

Figure 1:
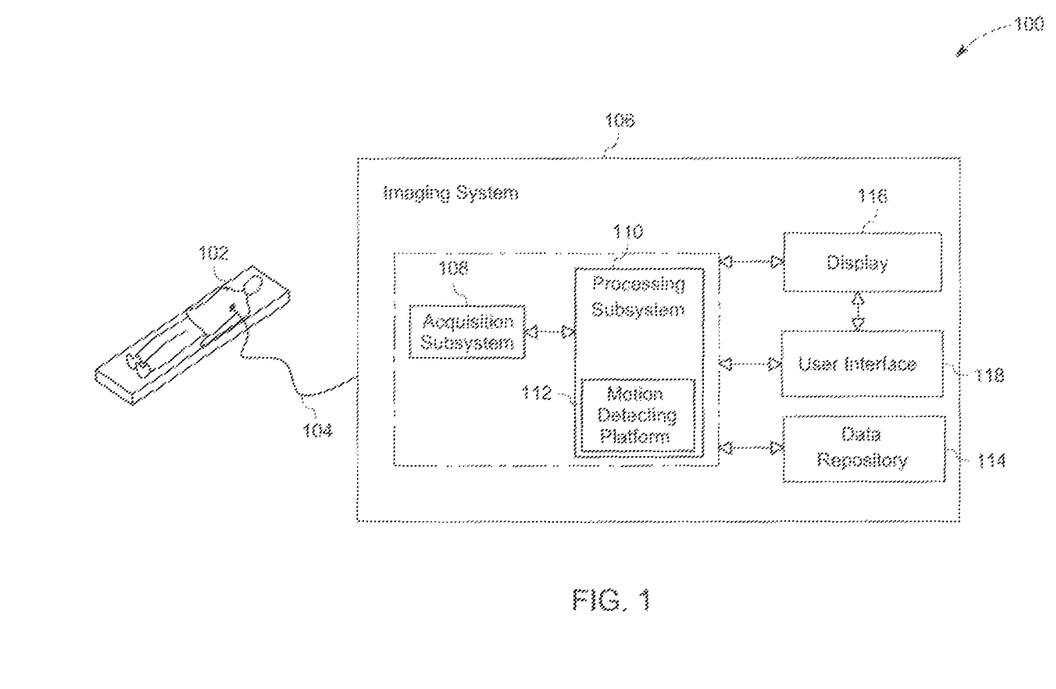
FIG. 1 is a diagrammatical illustration of a system for automated detection of motion, in accordance with aspects of the present specification.

FIG. 1 is a block diagram of an exemplary system 100 for use in diagnostic imaging, in accordance with aspects of the present specification. The system 100 is configured to aid a clinician such as a radiologist in automatically detecting patient motion, if any. More particularly, the system 100 may be configured to aid in enhancing clinical workflow by automatically detecting presence of motion and quantifying the extent of the detected motion. In addition, the system 100 may also be configured to facilitate determination of a suitable corrective course of action to correct the detected motion.

In one embodiment, the system 100 may be configured to acquire image data from a subject of interest such as a patient 102. In one embodiment, an image acquisition device 104 may be employed to acquire image data. However, other embodiments of the system 100 may obviate the need for use of the image acquisition device 104. The image acquisition device 104 may include a probe, where the probe may include an invasive probe, or a non-invasive or external probe that is configured to aid in the acquisition of image data. In certain other embodiments, image data may be acquired via one or more sensors (not shown) that may be disposed on the patient 102. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown), for example. Use of one or more detectors or detector arrays for acquiring image data is also envisaged.

The system 100 may also include a medical imaging system 106. In one embodiment, the medical imaging system 106 may be in operative association with the image acquisition device 104. Also, in the present example, the medical imaging system 106 may include a magnetic resonance imaging (MRI) system. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ magnetic resonance imaging (MRI) in conjunction with other imaging modalities, position-tracking systems or other sensor systems. For example, the multi-modality imaging system may include a positron emission tomography (PET) imaging system-MRI system. Furthermore, it should be noted that although the exemplary embodiments illustrated hereinafter are described in the context of a medical imaging system, such as MRI system, use of other imaging systems, such as, but not limited to, a computed tomography (CT) imaging system, a contrast enhanced ultrasound imaging system, an X-ray imaging system, an optical imaging system, a positron emission tomography (PET) imaging system, an ultrasound imaging system, a contrast enhanced X-ray imaging system, and other imaging systems is also contemplated in accordance with aspects of the present specification.

As noted hereinabove, in a presently contemplated configuration, the medical imaging system 106 is an MRI system. The medical imaging system 106 may include an acquisition subsystem 108 and a processing subsystem 110, in one embodiment. Further, the acquisition subsystem 108 of the medical imaging system 106 may be configured to acquire image data representative of one or more anatomical regions of interest in the patient 102 via the image acquisition device 104, in one embodiment. However, in certain other embodiments, the acquisition subsystem 108 may be configured to acquire image data without the use of the image acquisition device 104.

The system 100 and more particularly the acquisition subsystem 108 may be configured to acquire image data corresponding to an anatomical region of interest in the patient 102 in real-time. Alternatively, the plurality of images may be obtained by the acquisition subsystem 108 from an archival site, a database, or an optical data storage article. For example, the acquisition subsystem 108 may be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format.

In one example, the anatomical region of interest may include any tissue that can be perfused. Additionally, the anatomical region of interest may include any tissue that has a potential for perfusion deficit. Some non-limiting examples of the anatomical regions of interest include the breasts, the prostrate, bones, the kidneys, the lungs, or the uterus in the patient 102.

The acquired image data may include a plurality of images. Furthermore, the acquired image data may include a plurality of two-dimensional (2D) images acquired over time, where the plurality of 2D images corresponds to the anatomical region of interest being imaged. The acquired image data may also include three-dimensional (3D) images corresponding to the anatomical region of interest acquired over a period of time. It may be noted that the 3D images corresponding to the anatomical region of interest acquired over a period of time may be representative of four-dimensional (4D) images corresponding to the anatomical region of interest. It may also be noted that although the present specification is described in terms of 4D images, use of the present specification with images having higher or lower dimensions is also envisaged.

Moreover, in one embodiment, the acquired image data may be representative of dynamic data. In particular, the acquired image data may include contrast enhanced dynamic data. Accordingly, the acquisition of image data may entail acquiring one or more images accompanied with the use of a contrast agent. The contrast agent may include an endogenous contrast agent or an exogenous contrast agent.

It may be noted that in certain situations an exogenous contrast agent may be used. In such situations, one or more images of the plurality of images corresponding to the anatomical region of interest may be acquired prior to administering the exogenous contrast agent to the patient 102. The exogenous contrast agent may subsequently be administered to the patient 102. In one example, the contrast agent may include a gadolinium based contrast agent. One or more images may be acquired subsequent to the exogenous contrast agent being administered to the patient 102.

Furthermore, in situations where the endogenous contrast agent is utilized, the anatomical region of interest or a marker such as blood may be "prepared" for contrast. In one example, the marker such as blood may be prepared for contrast using magnetization. More particularly, blood may be magnetically labeled and the loss of magnetization may be tracked over time. In another example, the anatomical region of interest may be prepared for contrast via use of a genetic marker. In this example, the anatomical region of interest may be configured to provide contrast in response to a stimulus such as light.

Also, it may be noted that the dynamic data may include dynamic contrast enhanced images such as dynamic contrast enhanced (DCE) magnetic resonance images, dynamic susceptibility contrast (DSC) magnetic resonance images, arterial spin labeled (ASL) images, contrast enhanced X-ray images, contrast enhanced computed tomography (CT) images, contrast enhanced ultrasound images, or combinations thereof.

Additionally, the acquired image data may be processed by the processing subsystem 110. According to aspects of the present specification, the image data acquired and/or processed by the medical imaging system 106 may be employed to aid a clinician in detecting motion using the acquired plurality of images. In one example, the system 100 may be configured to aid in the automated detection of motion.

In certain embodiments, the processing subsystem 110 may be further coupled to a storage system, such as the data repository 114, where the data repository 114 may be configured to store the acquired and/or processed image data. Furthermore, the image data acquired by the acquisition subsystem 108 may be stored in the data repository 114 (see FIG. 1). In certain embodiments, the data repository 114 may include a local database.

Furthermore, in accordance with exemplary aspects of the present specification, the processing subsystem 110 may include a motion detecting platform 112 that is configured to aid in the automated detection of motion of the patient 102, if any, during the imaging procedure. More particularly, the motion detecting platform 112 may be configured to automatically detect motion using the acquired plurality of images. The motion detecting platform 112 may also be configured to aid in correcting the detected motion by compensating for the detected motion.

In addition, as illustrated in FIG. 1, the medical imaging system 106 may include a display 116 and a user interface 118. In certain embodiments, such as in a touch screen, the display 116 and the user interface 118 may overlap. Also, in some embodiments, the display 116 and the user interface 118 may include a common area. In accordance with aspects of the present specification, the display 116 of the medical imaging system 106 may be configured to display one or more images corresponding to the anatomical region of interest, an indicator of the detected motion generated by the medical imaging system 106, the corrected images, and the like.

Also, the user interface 118 of the medical imaging system 106 may include a human interface device (not shown) configured to aid the clinician in manipulating image data displayed on the display 116. The human interface device may include a mouse-type device, a trackball, a joystick, a stylus, or a touch screen configured to facilitate the clinician to identify the one or more regions of interest. However, as will be appreciated, other human interface devices, such as, but not limited to, a touch screen, may also be employed. Furthermore, in accordance with aspects of the present specification, the user interface 118 may be configured to aid the clinician in navigating through the images acquired by the medical imaging system 106. Additionally, the user interface 118 may also be configured to aid in manipulating and/or organizing the displayed images displayed on the display 116. The automated method of detecting patient motion using the acquired plurality of images will be explained in greater detail with reference to FIGS. 2-5.

Figure 2:
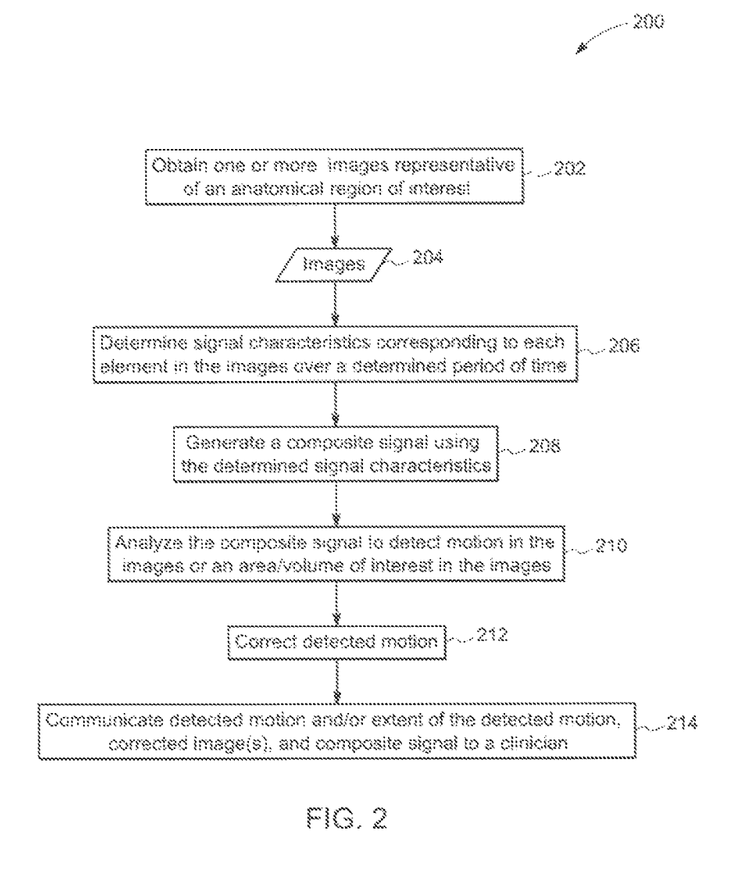
FIG. 2 is a flow chart depicting an exemplary method for automated detection of motion, in accordance with aspects of the present specification.

Turning now to FIG. 2, a flow chart of exemplary logic 200 for a method for automatically detecting motion using DCE MRI images, for example, is depicted. As previously noted, these DCE MRI images may correspond to an anatomical region of interest in a patient such as the patient 102 of FIG. 1. Furthermore, any patient motion may affect signal characteristics corresponding to the anatomical region of interest being imaged. It may be noted that the method of FIG. 2 is described in terms of the various components of FIG. 1.

The method 200 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, local to an imaging system 106 (see FIG. 1) and in operative association with a processing subsystem. In certain other embodiments, the computer executable instructions may be located in computer storage media, such as memory storage devices, that are removed from the imaging system. Moreover, the method for automated detection of motion includes a sequence of operations that may be implemented in hardware, software, or combinations thereof.

As will be appreciated during a typical scan session, a subject such as the patient 102 is positioned for imaging and the clinician attempts to image a desired anatomical region of interest in the patient. Accordingly, the patient may be positioned for imaging. Following any pre-imaging procedures, an anatomical region of interest for imaging may be selected. In one example, the clinician may identify the anatomical region of interest in the patient to be imaged. As previously noted, the anatomical region of interest may include any tissue that can be perfused or a tissue that has a potential for perfusion deficit. Some non-limiting examples of the anatomical regions of interest include the breasts, the prostrate, bones, the kidneys, the lungs, or the uterus in the patient. In certain other embodiments, the system 100 may be configured to automatically select the anatomical region of interest to be imaged based on the position of the patient in/on the imaging system, for example.

Subsequent to the selection of the anatomical region of interest, image data corresponding to the selected anatomical region of interest in the patient may be acquired. As previously noted, in one embodiment, the image data may be acquired in real-time. However, in certain other embodiments, previously acquired data may be retrieved from a data repository, such as the data repository 114. As previously noted, any motion experienced by the patient during the scanning procedure may adversely affect the quality of acquired image data corresponding to the anatomical region of interest being imaged. In particular, patient motion, if any, may alter the signal characteristics corresponding to the anatomical region of interest being imaged. Accordingly, in one embodiment, the signal characteristics corresponding to the anatomical region of interest being imaged may be monitored and evaluated to detect any patient motion.

Once the preliminary steps in the imaging process have been carried out, one or more images 204 corresponding to the selected anatomical region of interest in the patient may be acquired, as generally indicated by step 202. As previously noted, the one or more images 202 may include dynamic 2D images, dynamic 3D images, and/or 4D images. It may be noted that in the example of FIG. 2, the method is described with reference to the DCE MRI 4D images corresponding to the selected anatomical region of interest. Although the method of FIG. 2 is described in terms of automatically detecting motion using DCE MRI images, use of this method for automatically detecting motion using other images that include dynamic data is also envisaged. In addition, other images such as, but not limited to, DSC images, ASL images, contrast enhanced X-ray images, contrast enhanced CT images, contrast enhanced ultrasound images, or combinations thereof may also be used for automatically detecting motion.

As previously noted, the acquired image data may include contrast enhanced dynamic data. Accordingly, the acquisition of image data may entail the use of a contrast agent, where the contrast agent may be an endogenous contrast agent or an exogenous contrast agent. In situations that call for the use of the exogenous contrast agent, one or more images may be acquired prior to administering the exogenous contrast agent to the patient. Subsequently, the exogenous contrast agent may be administered to the patient. One or more images may then be acquired ensuing the administering of the exogenous contrast agent. However, in situations where the endogenous contrast agent is used, the anatomical region or interest may be prepared for contrast.

As previously noted, the acquisition of the images 204, especially 4D DCE MRI images, necessitates long scan times. Patients undergoing these long scans may experience voluntary and/or involuntary motion. The motion of the patient may adversely affect the quality of the acquired image data. It may therefore be desirable to detect the motion, in real-time, thereby supporting any remedial action to correct the detected motion. Additionally, use of the contrast agent may adversely affect the detection of motion as the uptake of the contrast agent may confound visual perception of motion. Accordingly, it is highly desirable to efficiently detect and correct any motion.

Moreover, as will be appreciated, patient motion affects signal characteristics over a period of time. In accordance with exemplary aspects of the present specification, signal characteristics corresponding to the anatomical region of interest being imaged may be monitored and evaluated to detect any perceptible patient motion. In one embodiment, the signal characteristics may be automatically analyzed to detect variations or deviations. These deviations may be indicative of abrupt patient motion corresponding to certain time phases. In addition, the extent of the deviations may be indicative of the extent of abrupt motion that has transpired in those phases.

To that end, at step 206, signal characteristics corresponding to the images 204 may be determined. More particularly, the signal characteristics corresponding to each element in the images 204 may be determined over a determined period of time. In one embodiment, the signal characteristics may include a magnetic resonance (MR) signal that has been modulated by contrast flow. Also, the elements in the images 204 may correspond to pixels or voxels in the images 204. Moreover, the determined period of time may correspond to the scan time.

Furthermore, a composite signal may be generated, as indicated by step 208. In particular, the composite signal may be generated using the signal characteristics corresponding to the images 204 determined at step 206. Moreover, in one embodiment, the composite signal may include a "cumulative aggregate" signal. In one example, the cumulative aggregate signal may include an aggregate of the signal characteristics over the determined period of time and corresponding to the entire image or voxel space. Other non-limiting examples of the cumulative aggregate signal may include a sum of the signal characteristics over the determined period of time and corresponding to the entire image or voxel space, a weighted sum of the signal characteristics over the determined period of time and corresponding to the entire image or voxel space, ordered statistics of the signal characteristics over the determined period of time and corresponding to the entire image or voxel space, or combinations thereof.

However, in certain other embodiments, it may be desirable to evaluate only a select portion of the images 204 to detect any motion in that selected portion. Accordingly, an area or volume of interest may be selected in the images 204. It may be noted that in one embodiment the area or volume of interest may be automatically selected by the system. Alternatively, in certain embodiments, the area or volume of interest may be manually prescribed by the clinician.

Once the desired area or volume of interest is selected, it may be desirable to segment that area or volume. In one embodiment, a mask may be generated to aid in delineating the selected area or volume of interest. By way of example, if the anatomical region of interest being imaged includes the chest region of the patient and it is desirable to evaluate only the area or volume corresponding to the breast region, then a mask corresponding to the breast may be generated. In certain embodiments, a previously generated and stored mask or atlas corresponding to the breast may be retrieved from a data repository, such as the data repository 114 of FIG. 1.

The image corresponding to the anatomical region of interest may then be processed via use of the mask to delineate the area or volume of interest. Once the selected area or volume of interest is segmented, a cumulative aggregate signal corresponding to the selected area or volume of interest may be generated. In one example, the cumulative aggregate signal may be generated by summing the signal characteristics over the determined period of time and corresponding to the area or volume of interest. As previously noted, patient motion may affect the signal characteristics corresponding to certain areas or volumes of interest more prominently than other areas or volumes. Accordingly, generating the cumulative aggregate signal corresponding to an area or volume of interest may enhance the effects of patient motion on the signal characteristics.

In accordance with further aspects of the present specification, other signal characteristics may also be garnered for the detection of motion. Some non-limiting examples of other signal characteristics may include the arterial input function (AIF) and/or the vascular input function (VIF). As will be appreciated, patient motion may also affect the characteristics of the AIF and/or VIF. Accordingly, the signal characteristics corresponding to the AIF and/or VIF of the patient may also be employed in the detection of motion. In one example the signal characteristics corresponding to the AIF and/or VIF of the patient may be compared with an atlas that includes one or more previously stored arterial input functions (AIFs) and/or vascular input functions (VIFs) to detect motion. It may be noted that in one example the atlas may include one or more AIFs and/or VIFs that have been derived from a group of subjects of interest. In certain other examples, the atlas may include one or more AIFs and/or VIFs that have been derived based on determined vessel regions such as the aorta. Use of the AIF and/VIF aids in detecting and/or quantifying the extent of motion of each of the different phases of the contrast uptake, such as an arrival phase, a peak phase, and a washout phase.

Furthermore, once the cumulative aggregate signal corresponding to either the entire image or the selected area or volume of interest in the image is generated, the cumulative aggregate signal may be analyzed to detect presence of patient motion, any, as depicted by step 210. It may be noted that typically, the signal characteristics that are representative of the MR signal modulated by the contrast flow tend to change in a smooth and continuous manner. In accordance with aspects of the present specification, the cumulative aggregate signal may be analyzed to determine presence of any deviations or changes in the smooth, continuous curvature of the cumulative aggregate signal. The deviations or non-conformities may be representative of motion experienced by the patient undergoing the scanning procedure.

In one embodiment, a gradient of the cumulative aggregate signal may be computed at various time points. These gradient values may then be evaluated to determine any deviations in the cumulative aggregate signal. Some examples of techniques that may also be used to determine the presence of deviations in the curvature of the cumulative aggregate signal may include curvature metrics corresponding to each point on the curve, distance metrics with standardized enhancement pattern curves, and the like.

Moreover, in accordance with further aspects of the present specification, the cumulative aggregate signal may also be compared to a corresponding model or atlas to determine any non-conformities in the curvature of the cumulative aggregate signal. The non-conformities may be representative of patient motion. It may be noted that the sensitivity of detection may vary based on the anatomical region of interest being imaged. Accordingly, one or more determined thresholds may be employed to aid in the detection of any deviations in the cumulative aggregate signal.

Consequent to the processing of steps 202-210, patient motion, if any, may be detected. Also, an anatomical region in the patient that is affect by the patient motion is known. Furthermore, in certain embodiments, an extent or intensity of motion experienced by the patient may also be determined. In one embodiment, the extent of the detected motion may be determined via use of one or more threshold values. The threshold values may be automatically determined by the system. Alternatively, the threshold values may be externally supplied. It may be noted that the threshold values may be dependent on a desired tolerance of the system.

In accordance with exemplary aspects of the present specification, a corrective course of action may be determined based on the detected motion. In particular, the detected motion may be corrected to enhance the quality of acquisition of image data. Accordingly, at step 212, any detected motion may be corrected. In one embodiment, the detected motion may be corrected in the image data by compensating for the detected motion. According to aspects of the present specification, based on the information related to the detected motion, the remedial actions for correcting or compensating for the detected motion may include rejecting image data corresponding to a particular phase, employing a suitable registration algorithm, or in an extreme scenario recommending acquisition of another scan.

As noted hereinabove, the anatomical region in the patient experiencing motion and the extent of detected motion are identified. Also, as previously noted, the sensitivity of detection may vary based on the anatomical region of interest being imaged. In accordance with aspects of the present specification, the correction of the detected motion may be tailored based on the extent of detected motion.

In one example, the extent of detected motion may be determined via use of the one or more threshold values. As previously noted, these threshold values may be automatically determined by the system or may be externally supplied. Additionally, the threshold values may be selected based on a desired tolerance of the system. In particular, the detected motion may be compared with the one or more threshold values to determine the extent of motion. Accordingly, based on a comparison with the threshold values, if it is determined that the extent of motion is within tolerable limits, the image data corresponding to the regions affected by the patient motion may be selectively interpolated. To that end, time phases corresponding to the regions affected by patient motion may be identified. Image data corresponding to these time phases may be rejected. Subsequently, suitable fitting algorithms may be employed to interpolate the image data corresponding to the time phases affected by patient motion. In one example, fitting algorithms such as, but not limited to, L1-norm based minimization techniques, independent component analysis based techniques, and the like may be used.

Additionally, if the extent of motion is within tolerable limits, then in one example, suitable registration techniques may be used to correct the detected motion. In another example, if the extent of motion is greater than the desired tolerance or exceed the threshold values, then the acquired image data may be rejected. Furthermore, in one example, a repeat scan may be recommended and image data may be reacquired. It may be noted that in this situation, image data corresponding to non-contrast regions may be reacquired.

Moreover, as indicated by step 214, one or more of the original image data, the signal characteristics, the cumulative aggregate signal, the detected motion, the corrected image, and the like may be communicated to a clinician. It may be noted that in certain embodiments, step 214 may be an optional step. In one embodiment, one or more of the original image data, the signal characteristics, the cumulative aggregate signal, the detected motion, and/or the corrected image may be communicated to the clinician by visualization on a display, such as the display 116 of FIG. 1. This visual display may aid the clinician in the diagnosis of any disease state of the patient. Alternatively, information related to one or more of the original image data, the signal characteristics, the cumulative aggregate signal, the detected motion, and/or the corrected image may be communicated to the clinician via other means such as an audio signal.

Figure 3:
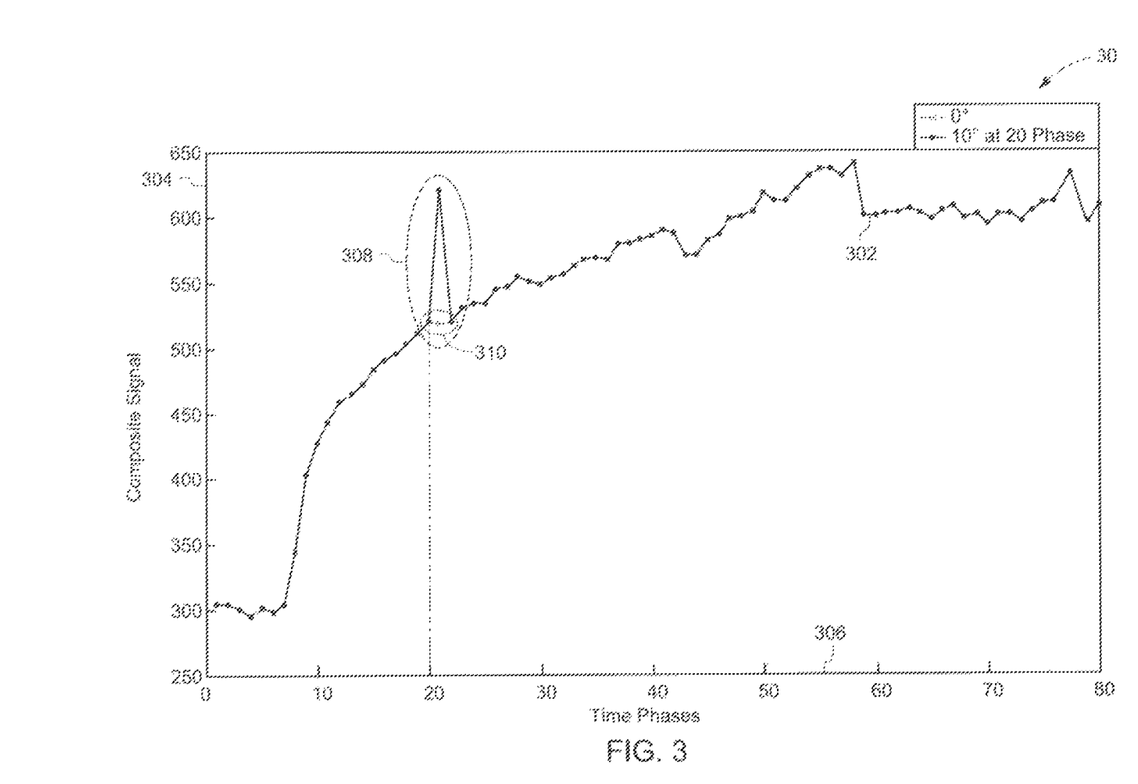
FIGS. 3-4 are diagrammatical representations of the exemplary method for automated detection of motion, in accordance with aspects of the present specification.
Figure 4:
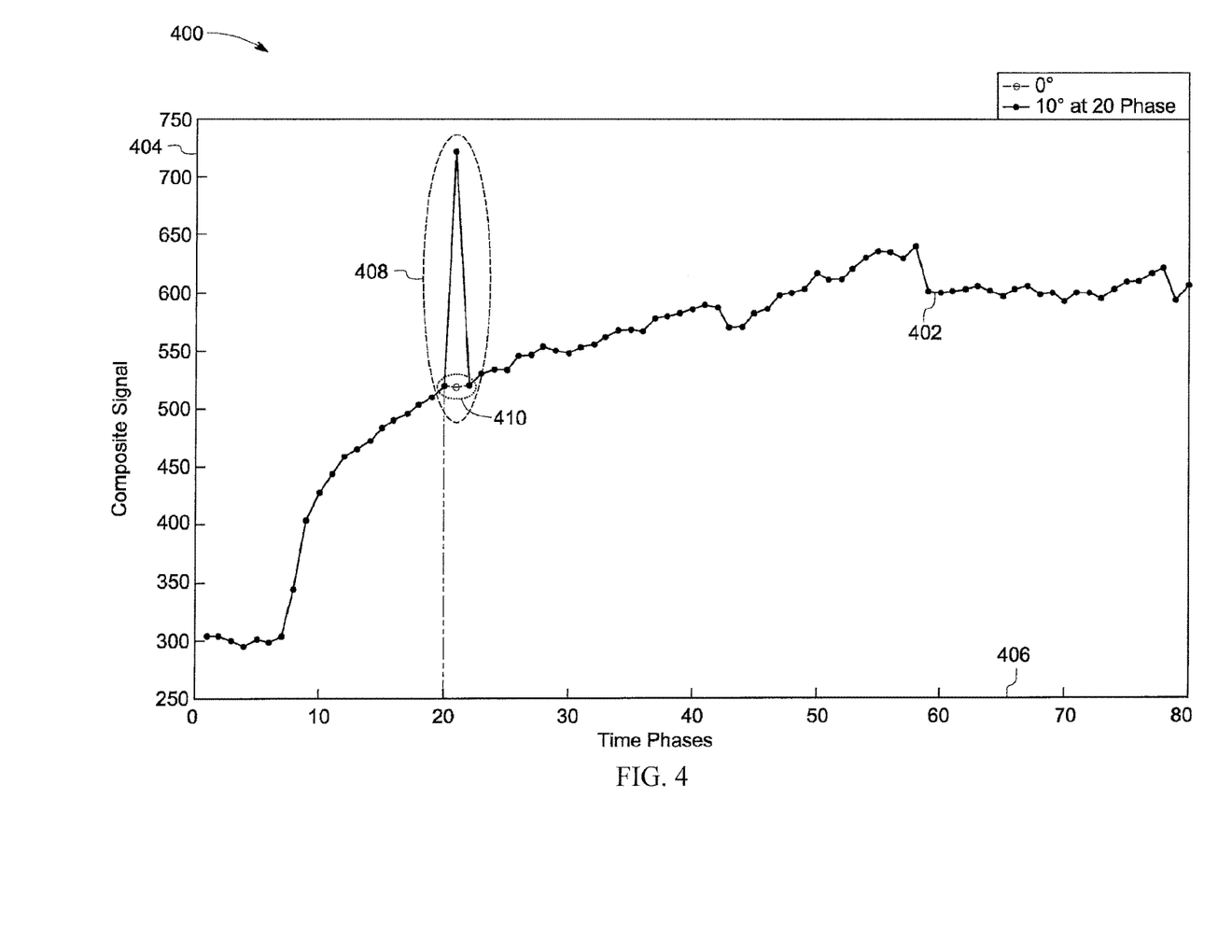

FIGS. 3-4 are diagrammatical representations of effects of motion on a composite signal such as a cumulative aggregate signal over a volume of interest when abrupt motions of different extents are induced during the scanning procedure. In the example of FIGS. 3-4, the volume of interest is generally representative of the prostrate in a patient. More particularly, in FIGS. 3 and 4, abrupt motions of different extents have been introduced in image data corresponding to a DCE MRI scan of the prostrate. Also, in the example of FIGS. 3 and 4, the motion induced includes a rotational motion.

FIG. 3 depicts a diagrammatical representation 300 of a cumulative aggregate signal corresponding to the prostrate, where a rotational motion of about 10 degrees has been induced in the DCE MRI scan. Reference numeral 302 is representative of a cumulative aggregate signal. Also, a value or amplitude of the cumulative aggregate signal 302 is represented by reference numeral 304, while reference numeral 306 is generally representative of a time phase of the cumulative aggregate signal 302. As depicted in FIG. 3, a variation 308 is detected at a time phase of about 20 due to the rotational motion of about 10 degrees induced in the DCE MRI scan. This variation 308 may be indicative of abrupt rotational motion in the patient. Once the motion and/or the extent of the motion are detected, corrective measures may be undertaken to obviate undesirable effects of the motion on the image data acquisition. Also, the time phase corresponding to the detected motion is identified. In accordance with aspects of the present specification, in the present example of FIG. 3, image data corresponding to the motion affected phase may be ignored and the image data corresponding to the affected region or phase may be interpolated, as generally indicated by reference numeral 310.

Referring now to FIG. 4, a diagrammatical representation 400 of another cumulative aggregate signal 402 corresponding to the prostrate, where a rotational motion of about 20 degrees has been induced in the DCE MRI scan is depicted. In FIG. 4, a value or amplitude of the cumulative aggregate signal 402 is represented by reference numeral 404 and reference numeral 406 is generally representative of a time phase of the cumulative aggregate signal 402. Reference numeral 408 is representative of the abrupt motion detected at a time phase of about 20 due to the rotational motion of about 20 degrees induced in the DCE MRI scan. The time phase corresponding to the detected motion is identified. Subsequent to the detection of the motion and the extent of the motion, corrective measure may be undertaken to obviate undesirable effects of the motion on the image data acquisition. In one example, image data corresponding to the motion affected phase may be ignored and the image data corresponding to the affected region or phase may be interpolated, as generally indicated by reference numeral 410.

As clearly evidenced by the examples of FIGS. 3 and 4, the extent of motion induced in the DCE MRI scans of the prostrate in the patient results in variations in the signal characteristics of the corresponding cumulative aggregate signals 302, 402. Moreover, as depicted in FIG. 3, a rotational motion of about 10 degrees induced in the DCE MRI scan results in a peak having an amplitude of about 100 at time phase 20. In a similar fashion, as depicted in FIG. 4, a rotational motion of about 20 degrees induced in the DCE MRI scan at time phase 20 results in a peak having an amplitude of about 200. FIGS. 3-4 clearly demonstrate that there are strong and abrupt changes in the signal characteristics in the phase corresponding to the occurrence of patient motion. In addition, the stronger abrupt motion of FIG. 4 results in stronger and sharper peak, while the abrupt motion of lower strength results in a peak of lower amplitude, thereby providing an indication of the extent of motion.

Figure 5:
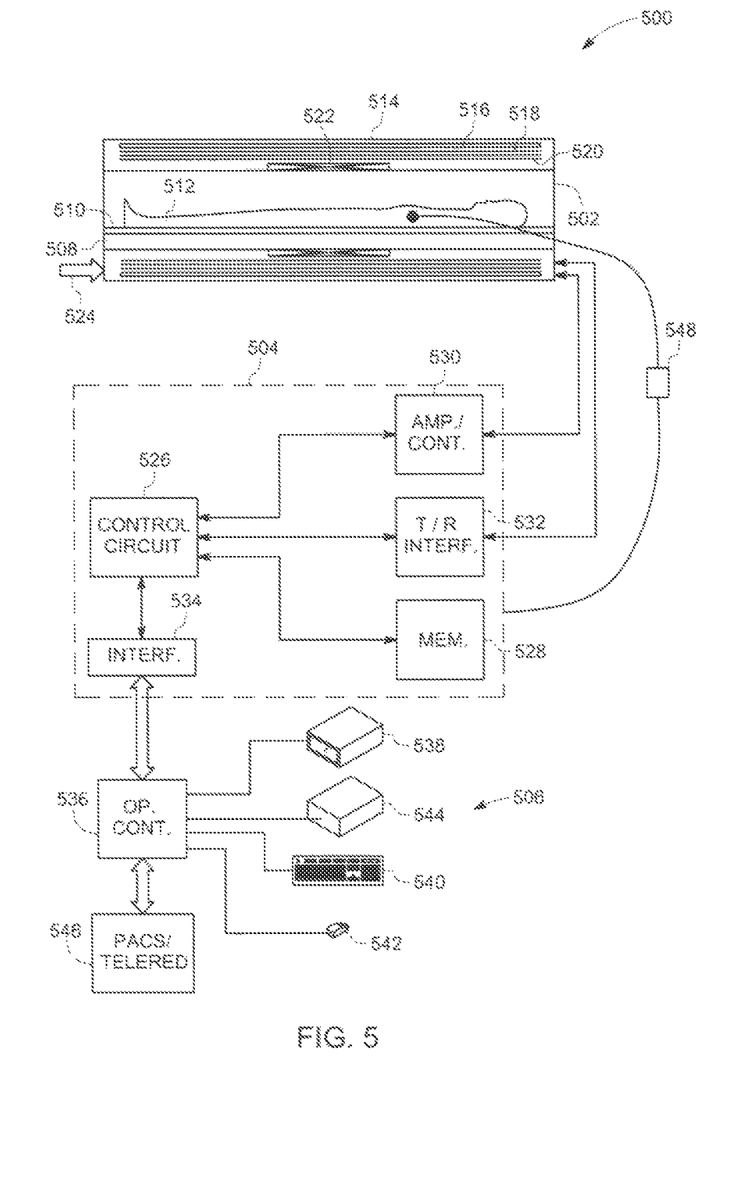
FIG. 5 is a diagrammatical illustration of a magnetic resonance imaging system for use in the system of FIG. 1.

As previously noted with reference to FIG. 1, the medical imaging system 106 may include a magnetic resonance imaging (MRI) imaging system. FIG. 5 is a block diagram of an embodiment of an MRI imaging system 500. The MRI system 500 is illustrated diagrammatically as including a scanner 502, scanner control circuitry 504, and system control circuitry 506. While the MRI system 500 may include any suitable MRI scanner or detector, in the illustrated embodiment the system includes a full body scanner including a patient bore 508 into which a table 510 may be positioned to place a patient 512, such as the patient 102 in a desired position for scanning. The scanner 502 may be of any suitable type of rating, including scanners varying from 0.5 Tesla ratings to 3 Tesla ratings and beyond.

Additionally, the scanner 502 may include a series of associated coils for producing controlled magnetic fields, for generating radio-frequency (RF) excitation pulses, and for detecting emissions from gyromagnetic material within the patient 512 in response to such pulses. In the diagrammatical view of FIG. 5, a primary magnet coil 514 may be provided for generating a primary magnetic field generally aligned with patient bore 508. A series of gradient coils 516, 518 and 520 may be grouped in a coil assembly for generating controlled magnetic gradient fields during examination sequences as will be described in greater detail hereinafter. A RF coil 522 may be provided for generating radio frequency pulses for exciting the gyromagnetic material. In the embodiment illustrated in FIG. 5, the coil 522 also serves as a receiving coil. Thus, the RF coil 522 may be coupled with driving and receiving circuitry in passive and active modes for receiving emissions from the gyromagnetic material and for applying RF excitation pulses, respectively. Alternatively, various configurations of receiving coils may be provided separate from the RF coil 522. Such coils may include structures specifically adapted for target anatomies, such as head coil assemblies, and so forth. Moreover, receiving coils may be provided in any suitable physical configuration, including phased array coils, and so forth.

In a presently contemplated configuration, the gradient coils 516, 518 and 520 may have different physical configurations adapted to their function in the imaging system 500. As will be appreciated by those skilled in the art, the coils include conductive wires, bars or plates that are wound or cut to form a coil structure that generates a gradient field upon application of control pulses as described below. The placement of the coils within the gradient coil assembly may be done in several different orders. In one embodiment, a Z-axis coil may be positioned at an innermost location, and may be formed generally as a solenoid-like structure that has relatively little impact on the RF magnetic field. Thus, in the illustrated embodiment, the gradient coil 520 is the Z-axis solenoid coil, while the coils 516 and 518 are Y-axis and X-axis coils respectively.

The coils of the scanner 502 may be controlled by external circuitry to generate desired fields and pulses, and to read signals from the gyromagnetic material in a controlled manner. As will be appreciated by those skilled in the art, when the material, typically bound in tissues of the patient, is subjected to the primary field, individual magnetic moments of the paramagnetic nuclei in the tissue partially align with the field. While a net magnetic moment is produced in the direction of the polarizing field, the randomly oriented components of the moment in a perpendicular plane generally cancel one another. During an examination sequence, an RF frequency pulse is generated at or near the Larmor frequency of the material of interest, resulting in rotation of the net aligned moment to produce a net transverse magnetic moment. This transverse magnetic moment precesses around the main magnetic field direction, emitting RF signals that are detected by the scanner 502 and processed for reconstruction of the desired image.

The gradient coils 516, 518 and 520 may be configured to serve to generate precisely controlled magnetic fields, the strength of which vary over a predefined field of view, typically with positive and negative polarity. When each coil is energized with known electric current, the resulting magnetic field gradient is superimposed over the primary field and produces a desirably linear variation in the Z-axis component of the magnetic field strength across the field of view. The field varies linearly in one direction, but is homogenous in the other two. The three coils have mutually orthogonal axes for the direction of their variation, enabling a linear field gradient to be imposed in an arbitrary direction with an appropriate combination of the three gradient coils.

The pulsed gradient fields perform various functions integral to the imaging process. Some of these functions are slice selection, frequency encoding and phase encoding. These functions may be applied along the X-axis, Y-axis and Z-axis of the original coordinate system or along other axes determined by combinations of pulsed currents applied to the individual field coils.

The slice select gradient determines a slab of tissue or anatomy to be imaged in the patient. The slice select gradient field may be applied simultaneously with a frequency selective RF pulse to excite a known volume of spins within a desired slice that is at the same frequency. The slice thickness is determined by the bandwidth of the RF pulse and the gradient strength across the field of view.

The frequency encoding gradient is also known as the readout gradient, and is usually applied in a direction perpendicular to the slice select gradient. In general, the frequency encoding gradient is applied before and during the formation of the magnetic resonance (MR) echo signal resulting from the RF excitation. Spins of the gyromagnetic material under the influence of this gradient are frequency encoded according to their spatial position along the gradient field. By Fourier transformation, acquired signals may be analyzed to identify their location in the selected slice by virtue of the frequency encoding.

Finally, the phase encode gradient is generally applied before the readout gradient and after the slice select gradient. Localization of spins in the gyromagnetic material in the phase encode direction may be accomplished by sequentially inducing variations in phase of the protons of the material using slightly different gradient amplitudes that are sequentially applied during the data acquisition sequence. The phase encode gradient permits phase differences to be created among the spins of the material in accordance with their position in the phase encode direction.

As will be appreciated by those skilled in the art, a great number of variations may be devised for pulse sequences employing the exemplary gradient pulse functions described hereinabove as well as other gradient pulse functions not explicitly described here. Moreover, adaptations in the pulse sequences may be made to appropriately orient both the selected slice and the frequency and phase encoding to excite the desired material and to acquire resulting MR signals for processing.

The coils of the scanner 502 are controlled by scanner control circuitry 504 to generate the desired magnetic field and RF pulses. In the diagrammatical view of FIG. 5, the control circuitry 504 thus includes a control circuit 526 for commanding the pulse sequences employed during the examinations, and for processing received signals. The control circuit 526 may include any suitable programmable logic device, such as a CPU or digital signal processor of a general purpose or application-specific computer. Also, the control circuit 526 may further include memory circuitry 528, such as volatile and non-volatile memory devices for storing physical and logical axis configuration parameters, examination pulse sequence descriptions, acquired image data, programming routines, and so forth, used during the examination sequences implemented by the scanner.

Interface between the control circuit 526 and the coils of the scanner 502 is managed by amplification and control circuitry 530 and by transmission and receive interface circuitry 532. The amplification and control circuitry 530 includes amplifiers for each gradient field coil to supply drive current to the field coils in response to control signals from control circuit 526. Transmit/receive (T/R) circuitry 532 includes additional amplification circuitry for driving the RF coil 522. Moreover, where the RF coil 522 serves both to emit the RF excitation pulses and to receive MR signals, the T/R circuitry 532 may typically include a switching device for toggling the RF coil between active or transmitting mode, and passive or receiving mode. A power supply, denoted generally by reference numeral 524 in FIG. 5, is provided for energizing the primary magnet 514. Finally, the scanner control circuitry 504 may include interface components 534 for exchanging configuration and image data with system control circuitry 506. It should be noted that, while in the present description reference is made to a horizontal cylindrical bore imaging system employing a superconducting primary field magnet assembly, the present technique may be applied to various other configurations, such as scanners employing vertical fields generated by superconducting magnets, permanent magnets, electromagnets or combinations of these means.

The system control circuitry 506 may include a wide range of devices for facilitating interface between an operator or radiologist and the scanner 502 via the scanner control circuitry 504. In the illustrated embodiment, for example, an operator controller 536 is provided in the form of a computer workstation employing a general purpose or application-specific computer. The workstation also typically includes memory circuitry for storing examination pulse sequence descriptions, examination protocols, user and patient data, image data, both raw and processed, and so forth. Further, the workstation may further include various interface and peripheral drivers for receiving and exchanging data with local and remote devices. In the illustrated embodiment, such devices include a conventional computer keyboard 540 and an alternative input device such as a mouse 542. A printer 544 may be provided for generating hard copy output of documents and images reconstructed from the acquired data. Moreover, a computer monitor 538 may be provided for facilitating operator interface. In addition, the system 500 may include various local and remote image access and examination control devices, represented generally by reference numeral 546 in FIG. 5. Such devices may include picture archiving and communication systems, teleradiology systems, and the like.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present MRI system 500 is provided by way of example, and the present specification is in no way limited by the specific system configuration.

In the example of FIG. 5, an exemplary motion detecting platform 548 such as the motion detecting platform 112 of FIG. 1 is shown as being operatively coupled to the MRI system 500. However, in certain other embodiments, the motion detecting platform 548 may be an integral part of the MRI system 500.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various systems and methods for automated detection of motion described hereinabove provide a framework for robust detection of any patient motion. Additionally, the framework enables the robust quantification of the extent of motion. Moreover, the systems and methods allow a quick estimation of the motion and/or extent of motion and this information regarding the detected motion may be communicated to the clinician. Furthermore, the systems and methods presented herein allow the automated detection and/or correction of motion, which in turn enhances the efficacy of the image data acquisition, while minimizing net scan time for the clinician, and thereby improving clinical workflow.

Determination of motion of organs such as the breast, the prostrate, bones, the kidneys, the lungs, the uterus, and the like is generally challenging. In addition, flow of contrast exacerbates the problem, thereby making it difficult for techniques such as subtraction of image slices to determine motion. The systems and methods described hereinabove circumvent the shortcomings of the presently available techniques and aid in determining motion in 4D dynamic contrast enhanced scans of the organs. In particular, the systems and methods aid in the detection and correction of motion in 4D contrast enhanced images of organs.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

We claim:

1. A method for automated detection of motion, the method comprising:
   identifying a region of interest in each of a plurality of images corresponding to a subject of interest;
   determining signal characteristics corresponding to the region of interest in each of the plurality of images;
   generating a cumulative aggregate signal which includes an aggregate of the signal characteristics corresponding to the region of interest in each of the plurality of images; and
   analyzing the cumulative aggregate signal to detect motion in the region of interest.

2. The method of claim 1, wherein the plurality of images comprise dynamic two-dimensional images, dynamic three-dimensional images, or a combination thereof.

3. The method of claim 2, wherein the plurality of images comprise dynamic contrast enhanced images.

4. The method of claim 1, further comprising obtaining the plurality of images corresponding to the subject of interest.

5. The method of claim 4, further comprising administering a contrast agent to the subject, wherein the contrast agent comprises an endogenous contrast agent, an exogenous contrast agent, or a combination thereof.

6. The method of claim 5, wherein obtaining the plurality of images comprises acquiring one or more images prior to administering the contrast agent to the subject.

7. The method of claim 6, wherein obtaining the plurality of images further comprises acquiring one or more images after administering the contrast agent to the subject.

8. The method of claim 6, wherein the signal characteristics comprise a magnetic resonance signal modulated by a contrast flow.

9. The method of claim 1, wherein determining the signal characteristics comprises computing signal characteristics corresponding to each element in the region of interest across a determined period of time.

10. The method of claim 1, further comprising analyzing the cumulative aggregate signal to detect motion in the region of interest by automatically detecting a deviation in the cumulative aggregate signal.

11. The method of claim 10, wherein the deviation is indicative of motion in the region of interest.

12. The method of claim 10, wherein detecting the deviation comprises automatically determining the deviation using one or more thresholds, an atlas, or a combination thereof.

13. The method of claim 10, further comprising analyzing an arterial input function or a vessel input function to detect motion in the region of interest.

14. The method of claim 10, wherein detecting the deviation comprises automatically determining the deviation by computing derivatives of the cumulative aggregate signal.

15. The method of claim 10, further comprising determining an extent of the deviation, wherein the extent of the deviation is indicative of an extent of the detected motion of the region of interest.

16. The method of claim 1, further comprising correcting the detected motion.

17. The method of claim 16, wherein correcting the detected motion comprises identifying a phase corresponding to the detected motion.

18. The method of claim 17, further comprising:
rejecting image data corresponding to the identified phase; and
interpolating image data corresponding to the identified phase to correct the detected motion.

19. The method of claim 1, further comprising communicating the detected motion, the extent of the detected motion, the cumulative aggregate signal, a corrected motion, or combinations thereof to a clinician.

20. The method of claim 19, wherein communicating the detected motion, the extent of the detected motion, the composite signal, the corrected motion, or combinations thereof to the clinician comprises visualizing the detected motion, the extent of the detected motion, the composite signal, the corrected motion, or combinations thereof on a display, generating an indicator representative of the detected motion, the extent of the detected motion, the composite signal, the corrected motion, or a combination thereof.

21. A system for automated detection of motion, the system comprising:
a motion detecting platform configured to:
identify a region of interest in each of a plurality of images corresponding to a subject of interest;
determine signal characteristics corresponding to the region of interest in each of the plurality of images;
generate a cumulative aggregate signal which includes an aggregate of the signal characteristics corresponding to the region of interest in each of the plurality of images;
analyze the cumulative aggregate signal to detect motion in the region of interest; and
correct the detected motion.

22. An imaging system, comprising:
an acquisition subsystem configured to acquire image data corresponding to a subject of interest;
a processing subsystem in operative association with the acquisition subsystem and configured to process the acquired image data, wherein the processing subsystem comprises a motion detecting platform configured to:
identify a region of interest in each of a plurality of images corresponding to a subject of interest;
determine signal characteristics corresponding to the region of interest in each of the plurality of images;
generate a cumulative aggregate signal which includes an aggregate of the signal characteristics corresponding to the region of interest in each of the plurality of images; and
analyze the cumulative aggregate signal to detect motion in the region of interest.

23. The imaging system of claim 22, wherein the motion detecting platform is further configured to correct the detected motion.

24. The imaging system of claim 22, wherein the imaging system is a magnetic resonance imaging system, an ultrasound imaging system, a contrast enhanced ultrasound imaging system, an optical imaging system, an X-ray imaging system, a computed tomography imaging system, a positron emission tomography imaging system, or combinations thereof.

25. The method of claim 1, wherein the aggregate of the signal characteristics is a sum or weighted sum of the signal characteristics.

* * * * *